United States Patent

Atkins

3,996,276
Dec. 7, 1976

[54] BICYCLIC AND TRICYCLIC PHOSPHOROUS TRIAMIDES

[75] Inventor: Thomas Joseph Atkins, Wilmington, Del.

[73] Assignee: E. I. Du Pont de Nemours and Company, Wilmington, Del.

[22] Filed: Aug. 22, 1975

[21] Appl. No.: 606,778

[52] U.S. Cl. .................. 260/551 P; 106/15 FP; 260/333; 260/338; 260/239 BC
[51] Int. Cl.² ................. C07F 9/02; C07F 9/22; C07D 255/00
[58] Field of Search ............ 260/551 P, 239 BC

[56] References Cited

OTHER PUBLICATIONS

Clardy et al., CA 81: 112283y (1974).
Mosbo et al., CA 77: 170976e (1972).
Stetter et al., CA 79: 146492q (1973).

*Primary Examiner*—Robert V. Hines
*Assistant Examiner*—Thomas A. Waltz

[57] ABSTRACT

Polycyclic phosphorous triamides of the formula

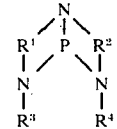

in which
R¹ and R², alike or different, are alkylene of 2 to 6 carbons;
R³ and R⁴, alike or different, are alkyl of 1 to 8 carbons, cycloalkyl of 5 to 8 carbons, or aralkyl where the aryl group is of 6 to 12 carbons and the alkyl is of 1 to 8 carbons; or R³ and R⁴ are joined together to form an alkylene group of 2 to 6 carbons which may be interrupted by
1. a

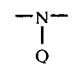

group where Q is hydrogen or alkyl of 1 to 18 carbons, or
2. one or two —O— linkages; there are at least 2 carbons between each two hetero atoms in the outer ring system, and when the triamide is tricyclic, at least one of the chains between the nitrogens linked to phosphorus contains at least three atoms are useful as flame retardants for cotton.

7 Claims, No Drawings

BICYCLIC AND TRICYCLIC PHOSPHOROUS TRIAMIDES

BACKGROUND OF THE INVENTION

This invention relates to polycyclic amides of phosphorous acid. More specifically, it relates to bicyclic and tricyclic triamides of phosphorous acid and their use as flame retardants for cotton.

Polycyclic phosphorous triamides and their carbon analogs are known, but no phosphorous triamides in which the amide nitrogens are annular hetero atoms in a single large ring are known. The closest prior art references are:

1. Stetter and Bremen, Chem. Ber., 106, 2523 (1973), disclose the following reaction:

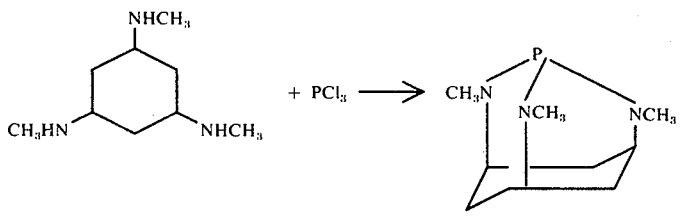

2. Laube et al., Inorg. Chem., 6, 173 (1967), disclose the transamidation reaction

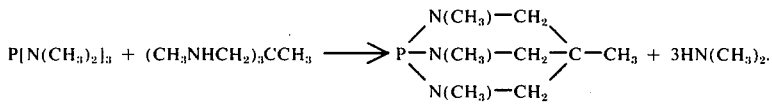

3. Petrov et al., U.S.S.R. 144,172 (1962) (C.A., 57, 5583 (1962)), disclose transamidation of phosphorous amides by heating with amines of higher boiling point than those of the amines that composed the amide groups of the initial amides.

SUMMARY OF THE INVENTION

In accordance with this invention, polycyclic phosphorous triamides have been discovered which are of the formula:

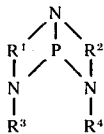

in which
R$^1$ and R$^2$, alike or different are alkylene of 2 to 6 carbons containing at least 2 carbons in the backbone, and
R$^3$ and R$^4$, alike or different, or alkyl of 1 to 8 carbons, cycloalkyl of 5 to 8 carbons, or aralkyl where the aryl group is of 6 to 12 carbons and the alkyl is of 1 to 8 carbons, or
R$^3$ and R$^4$ are joined together to form a divalent group selected from the group consisting of alkylene of 2 to 6 carbons containing at least 2 carbons in the backbone, $$-R^5-N-R^6-,$$
$$\quad\quad\;\;|$$
$$\quad\quad\;\;Q$$

—R$^5$—O—R$^6$—, and —R$^5$—O—R$^6$—O—R$^7$ where
R$^5$, R$^6$ and R$^7$, alike or different, are alkylene of 2 to 6 carbons containing 2 to 3 carbons in the backbone, and
Q is hydrogen or alkyl of 1 to 18 carbons,
and when the triamide is tricyclic, at least one of the chains between the nitrogens linked to phosphorus contains at least three atoms in the backbone.

DETAILED DESCRIPTION OF THE INVENTION

The compounds of this invention are bicyclic phosphorous triamides of the formula

and, when R$^3$ and R$^4$ are joined together to form an alkylene group or interrupted alkylene group, the compounds are tricyclic phosphorous triamides of the formula

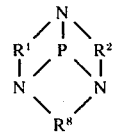

Examples of suitable R$^3$ and R$^4$ groups include alkyl such as methyl, propyl, t-butyl, and 1-ethyl-3-methylpentyl; cycloalkyl such as cyclopentyl and 2-methylcyclohexyl; and aralkyl such as benzyl, 1-naphthylmethyl, 1-methylphenethyl, and 7-phenylheptyl.

Suitable examples of R$^1$, R$^2$, and R$^8$ include ethylene, trimethylene, tetramethylene, pentamethylene, hexamethylene, 1,2-dimethylethylene, 2,2-dimethyltrimethylene, and 1,3,3-trimethyltrimethylene. In compounds of formula (1) R$^1$ and R$^2$ are usually ethylene, —CH$_2$CH$_2$—, because of availability of the starting materials. When the compound is of formula (2), suitable examples of R$^8$ also include 3-azapentamethylene, 3-methyl-3-azapentamethylene, 3-octadecyl-3-azapentamethylene, 3-oxapentamethylene, and 3,6-dioxaoctamethylene.

Because it makes the products of formula (2) easier to form, at least one of $R^1$, $R^2$, and $R^8$ should contain at least three atoms in the backbone. When $R^8$ is of the formula

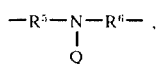

suitable examples of Q include hydrogen, methyl, ethyl, isopropyl, t-butyl, isopentyl, 2-ethylhexyl, dodecyl and octadecyl. Preferably Q is hydrogen or a $C_1$ to $C_8$ alkyl group.

The products of the invention are prepared by reacting the appropriate polyamine with a hexa(lower alkyl)phosphorous triamide (also known as a tris[di(lower alkyl)amino]phosphine). The process can be represented by the following equation:

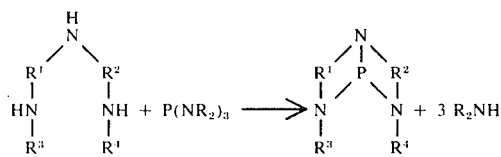

The chemical reaction involved is a transamidation, or amine exchange. The boiling point of the resulting di(lower alkyl) amine, $R_2NH$, should be lower than that of either of the starting materials or of the polycyclic triamide product.

Suitable 1,7-dihydrocarbyldialkylenetriamines of the formula $R^3$—NH—$R^1$—NH—$R^2$—NH—$R^4$ for forming the bicyclic triamides of formula (1) are known, for example, 1,7-dimethyldiethylenetriamine, 1,7-bis(1-methylheptyl) diethylenetriamine, 1,7-dicyclopentyldiethylenetriamine, and 1,7-dibenzyldiethylenetriamine. These starting materials may be prepared by known alkylation methods such as reductive amination of an aldehyde or ketone. Reductive amination with an aldehyde is carried out in accordance with the equation:

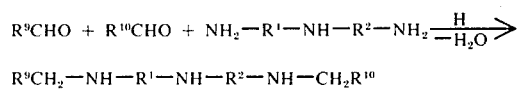

where $R^9CH_2$— and $R^{10}CH_2$— are $R^3$ and $R^4$ respectively.

Diethylenetriamine can be prepared by known methods. The higher dialkylenetriamines may be prepared by adaptations of these methods.

The cyclic polyamines used as starting materials for preparing the tricyclic triamides of formula (2) are prepared by the method outlined by Richman and Atkins in J. Amer. Chem. Soc., 96, 2268 (1974). Suitable examples of these cyclic polyamines include 1-oxa-4,7,10-triazacyclododecane, 1,4-dioxa-7,10,13-triazacyclopentadecane, 1,4,7-triazacyclodecane, 1,5,9-triazacyclododecane, 1,8,15-triazacycloheneicosane, 1,4,8-triazacycloundecane, and 1,4,7,10-tetraazacyclododecane.

Hexamethylphosphorous triamide is the preferred triamide starting material, since it is commercially available and the resulting dimethylamine, bp 7° C, is easily eliminated from the reaction mixture.

The products of the invention are colorless, crystalline solids or colorless liquids that can be purified by sublimation and/or distillation. They are hydrolyzed by water and react slowly with atmospheric moisture and oxygen at room temperature. These products are useful as flame retardants for cellulosics such as cotton.

EXAMPLES OF THE INVENTION

The following examples illustrate the invention. All preparations were carried out in an atmosphere of nitrogen. Mass-spectral analyses were relied on to confirm the empirical formulas of the products.

EXAMPLE 1

10-Oxa-1,4,7-triaza-13-phosphatricyclo[5.5.1.0$^{4,13}$]-tridecane is prepared as follows:

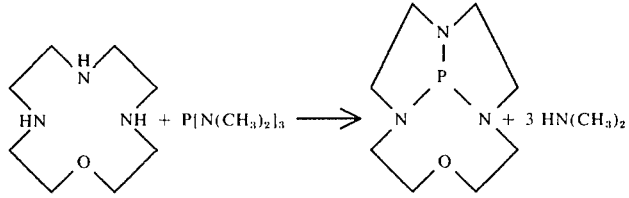

A. A solution of 2.50 g of 1-oxa-4,7,10-triazacyclododecane and 2.35 g of hexamethylphosphorous triamide in 25 ml of toluene is refluxed for forty hours. It is then concentrated to dryness in a rotary evaporator, to give 2.97 g (100%) of 10-oxa-1,4,7-triaza-13-phosphatricyclo[5.5.1.0$^{4,13}$]tridecane as a brittle, white solid. Sublimation at 80° C (0.007 mm) gives 2.08 g of white crystals having a melting point of 68°–70° C.

An infrared absorption spectrum of this material in mineral oil shows absorptions at 3.5, 6.82, 7.38, 7.59, 8.00, 8.24, 8.50, 8.83, 9.69, 9.89, 10.55, 11.18, 11.77, and 12.56μ.

B. 10-Oxa-1,4,7-triaza-13-phosphatricyclo[5.5.1.0$^{4,13}$]tridecane is obtained in the absence of a solvent by heating 10.0 g of 1-oxa-4,7,10-triazatricyclododecane and 9.40 g of hexamethylphosphorous triamide at 75° C for 2 hours, by which time evolution of dimethylamine is complete. The product is sublimed at 80° C (0.40 mm) and identified by comparison of its infrared absorption spectrum with that of the product of part A. Mass-spectral analysis of this sample shows an M$^+$ ion at 201; measured mass, 201.1094; calc'd 201.1031; which confirms the empirical formula of the product of part A.

If 1,4-dioxa-7,10,13-triazacyclopentadecane were used in place of 1-oxa-4,7,10-triazacyclododecane in essentially the procedure of Example 1, the product would be

EXAMPLE 3

1,5,9-Triaza-13-phosphatricyclo[7.3.1.0^{5,13}]tridecane is prepared as follows:

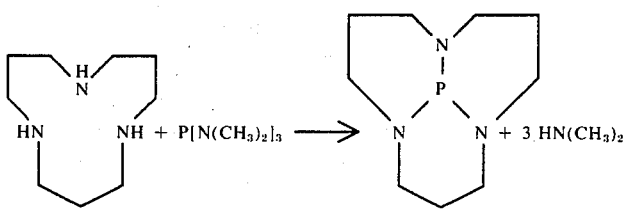

A mixture of 4.20 g of 1,5,9-triazacyclododecane and 4.00 g of hexamethylphosphorous triamide is heated at 100° C for about six hours, by which time evolution of dimethylamine is complete. Distillation under reduced pressure gives 3.70 g (76%) of 1,5,9-triaza-13-phosphatricyclo-[7.3.1.0$^{5,13}$]tridecane as a clear, colorless liquid which boils at 104°–135° C at 0.60 mm. The product solidifies at room temperature. Its infrared absorption spectrum (neat) shows absorptions at 3.5,

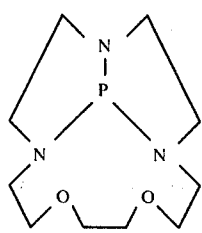

EXAMPLE 2

1,4,7-Triaza-11-phosphatricyclo[5.3.1.0$^{4,11}$]undecane is prepared as follows:

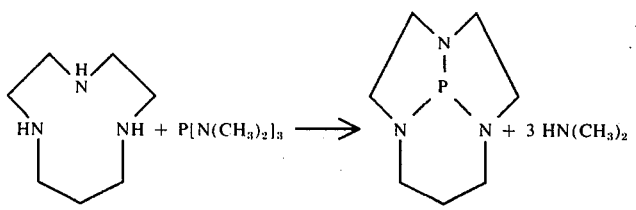

A. A solution of 5.00 g of 1,4,7-triazacyclodecane and 5.70 g of hexamethylphosphorous triamide in 50 ml. of toluene is refluxed for 48 hours. The toluene is removed under reduced pressure, and the residue is distilled through a short-path column, to give 5.31 g (89%) of 1,4,7-triaza-11-phosphatricyclo[5.3.1.0$^{4,1-1}$]undecane as a clear, colorless liquid having a boiling point of 96°–98° C at 0.70 mm. The product solidifies on standing at room temperature.

The infrared absorption spectrum (neat) of the product has absorptions at 3.5, 6.77, 7.01, 7.50, 7.78, 8.00, 8.24, 8.50, 8.78, 8.91, 9.12, 9.83, 10.10, 10.30, 10.8, 11.4, 12.4, and 12.8 $\mu$.

B. 1,4,7-Triaza-11-phosphatricyclo[5.3.1.0$^{4,11}$]undecane is prepared in the absence of a solvent by heating the reactants of part A at 75° C for 1.5 hours, during which time dimethylamine is evolved. Distillation gives 5.48 g (92%) of the desired product which boils at 84°–86° C at 0.30 mm. The product is identified by comparison of its infrared absorption spectrum with that of the product of part A. Mass-spectral analysis shows an M$^+$ ion at 171; measured mass, 171.0944; calc'd, 171.0925; which confirms the empirical formula of the product of part A.

6.85, 7.01, 7.52, 7.73, 8.00, 8.27, 8.66, 8.90, 9.02, 9.36, 9.56, 10.27, 10.89, 11.42, 11.73, 11.97 and 14.7 $\mu$. The mass spectrum shows an M$^+$ ion at 199; measured mass, 199.1264; calc'd, 199.1238.

If 1,8,15-triazacycloheneicosane were used in place of 1,5,9-triazacyclododecane in essentially the procedure of Example 3, the product would be

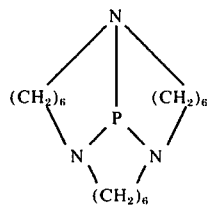

EXAMPLE 4

1,4,8-Triaza-12-phosphatricyclo[6.3.1.0$^{4,12}$]dodecane is prepared as follows:

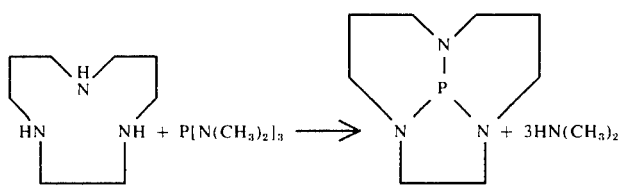

A mixture of 3.62 g of 1,4,8-triazacycloundecane and 3.75 g of hexamethylphosphorous triamide is heated to 125° C with stirring and held at this temperature for 2 hours, by which time evolution of dimethylamine is complete. Evolution is vigorous for the first 45 minutes. Distillation affords 3.20 g (75%) 1,4,8-triaza-12-phosphatricyclo-[6.3.1.0$^{4,12}$]dodecane as a water-white liquid which boils at 73°–75° C at 0.30 mm.

The infrared absorption spectrum (neat) of the product has absorptions at 3.5, 7.46, 7.51, 8.00, 8.23, 8.70, 8.82, 8.96, 9.31, 9.78, 10.05, 10.5, 11.5, 11.7, and 14.4 μ. The mass spectrum shows an M$^+$ ion at 181; measured mass, 181.1117; calc'd 181.1082.

EXAMPLE 5

2,8-Dimethyl-2,5,8-triaza-1-phosphabicyclo[3.3.0]-octane is prepared as follows:

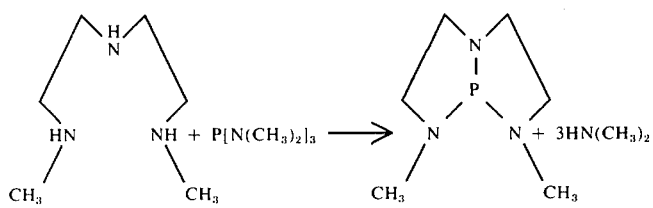

A mixture of 5.00 g of 1,7-dimethyldiethylenetriamine and 6.22 g of hexamethylphosphorous triamide is heated to 80° C, at which temperature dimethylamine begins to be evolved. Evolution of dimethylamine continues for about one hour, during which time the temperature is gradually raised to 125° C. The mixture is distilled to give 5.75 g (95%) of 2,8-dimethyl-2,5,8-triaza-1-phosphabicyclo[3.3.0]octane as a clear, colorless liquid, which boils at 55°–65° C at 0.30 mm. The nuclear magnetic-resonance spectrum (C$_6$D$_6$/TMS) of the product shows a highly split pattern from δ 2.0 to 4.5 and has the expected sharp doublet for the —CH$_3$ groups at δ 2.55, J = 10 Hz. The infrared absorption spectrum (neat) has absorptions at 3.5, 6.83, 6.91, 7.65, 7.80, 8.20, 8.68, 9.20, 9.70, 10.15, 10.4, 10.7, and 11.5 μ.

On standing overnight at room temperature, the product turns into an immobile glass. This transformation can be inhibited by storage at a sufficiently low temperature.

If 1,7-dicyclopentyldiethylenetriamine were substituted for 1,7-dimethyldiethylenetriamine in essentially the procedure of Example 5, the product would be

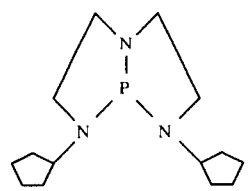

If 1,7-dibenzyldiethylenetriamine were substituted for 1,7-dimethyldiethylenetriamine in essentially the procedure of Example 5, the product would be 2,8-dibenzyl-2,5,8-triaza-1-phosphabicyclo[3.3.0]octane.

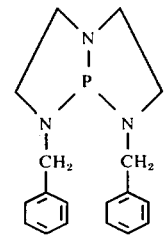

EXAMPLE 6

1,4,7,10-Tetraaza-13-phosphatricyclo[5.5.1.0$^{4,13}$]-tridecane is prepared as follows:

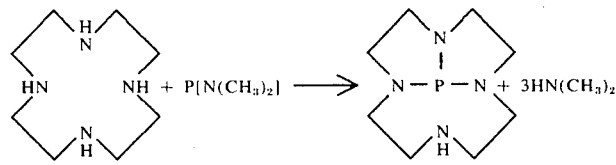

A. A solution of 1.75 g of 1,4,7,10-tetraazacyclodecane and 1.63 g of hexamethylphosphorous triamide in 50 ml of toluene is refluxed for 12 hours. Titration of the off-gases with 1 N HCl indicates that 97% of the theoretical amount of dimethylamine is evolved in this time. The toluene is removed under reduced pressure to give 2.0 g of 1,4,7,10-tetraaza-13-phosphatricyclo[5.5.1.0$^{4,13}$]tridecane as a white solid which melts at 109°–111° C with sintering from 90° C (possibly because of the presence of a trace of toluene). Sublimation of this product at 75° C and 0.55 mm gives large colorless crystals, which melt at 111°–113° C. The mass spectrum shows an M$^+$ ion at 200; measured mass, 200.1194; calc'd, 200.1190.

B. 1,4,7,10-Tetraaza-13-phosphatricyclo[5.5.1.0$^{4,13}$]tridecane is prepared in the absence of a solvent by heating 5.0 g of 1,4,7,10-tetraazacyclododecane and 4.7 g of hexamethylphosphorous triamide together at about 75° C for between two and three hours and subliming the crude product at 75° C at 0.4 mm. The yield is 5.3 g (92%) of product melting at 106°–108° C.

The infrared absorption spectrum of the product in mineral oil has absorptions at 3.05 (very weak), 4.31, 7.51, 8.00, 8.20, 8.36, 8.92, 9.50, 10.22, 10.5, 11.5, 13.4 and 14.6 $\mu$.

Measured mass (mass spec): 200.1226.

The infrared absorption of the product shows that it exists in tautomeric equilibrium with the structure

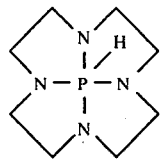

If 1-ethyl-1,4,7,10-tetraazacyclododecane were used in place of 1,4,7,10-tetraazacyclododecane in essentially the procedure of Example 6, the product would be of the formula

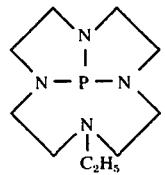

If 2,2,4,10,10,12-hexamethyl-1,5,9,13-tetraazacyclohexadecane were the starting material, the product would be of formula

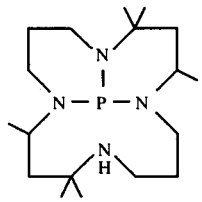

The products of the invention are useful as flame-retarding agents for cotton articles, as shown in the following examples.

EXAMPLE A

Solutions of the products of Examples 1 and 6 in dimethylformamide (10 weight/volume %) are prepared. Cotton swabs are soaked in these solutions for ten minutes and for 1 hour and dried overnight. Both the treated swabs and an untreated control are tested for flammability by holding them to a flame. The untreated control burns completely and glows after the flame extinguishes. All the treated swabs are self-extinguishing when removed from the flame; the swabs themselves are charred.

EXAMPLE B

Strips of cotton cloth are soaked overnight in 10 weight/volume % solutions of the products of Examples 1 and 6 in dimethylformamide and then dried. The treated fabrics, together with an untreated control, are tested for flammability by being held vertically and touched with a flame at their bottoms. The untreated control burns profusely. The fabric treated with the product of Example 1 self-extinguishes in less than one second and burns less than 5% of its length. The fabric treated with the product of Example 6 self-extinguishes in about one second and also burns about 5% of its length.

What is claimed is:
1. Polycyclic phosphorous triamides of the formula

in which
R$^1$ and R$^2$, alike or different, are alkylene of 2 to 6 carbons containing at least 2 carbons in the backbone, and
R$^3$ and R$^4$, alike or different, are alkyl of 1 to 8 carbons, cycloalkyl of 5 to 8 carbons, or aralkyl where the aryl group is of 6 to 12 carbons and the alkyl is of 1 to 8 carbons, or
R$^3$ and R$^4$ are joined together to form an alkylene radical of 2 to 6 carbons containing at least 2 carbons in the backbone,
and, when the triamide is tricyclic, at least one of the chains between the nitrogens linked to phosphorus contains at least three carbons in the backbone.
2. The bicyclic phosphorous triamides of claim 1 in which R$^1$ and R$^2$ are ethylene.
3. The bicyclic phosphorous triamide of claim 2 in which R$^3$ and R$^4$ are methyl.
4. The tricyclic phosphorous triamides of claim 15 of the formula

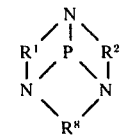

in which R$^1$, R$^2$, and R$^8$, alike or different, are alkylene of 2 to 3 carbons.
5. The tricyclic phosphorous triamide of claim 4 of the formula 6. The tricyclic phosphorous triamide of claim 4 of the formula
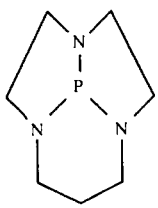
7. The tricyclic phosphorous triamide of claim 4 of the formula
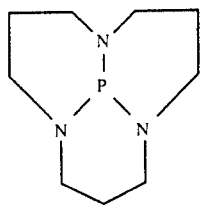
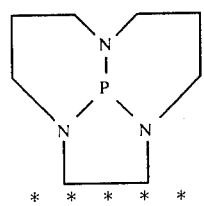
* * * * *

UNITED STATES PATENT OFFICE
CERTIFICATE OF CORRECTION

Patent No. 3,996,276      Dated December 7, 1976

Inventor(s) Thomas Joseph Atkins

It is certified that error appears in the above-identified patent and that said Letters Patent are hereby corrected as shown below:

Column 10, line 54, in Claim 4, line 1, "Claim 15"

should read -- Claim 1 --.

Signed and Sealed this

Nineteenth Day of April 1977

[SEAL]

Attest:

RUTH C. MASON
*Attesting Officer*

C. MARSHALL DANN
*Commissioner of Patents and Trademarks*